United States Patent
Cao et al.

(10) Patent No.: US 10,588,645 B1
(45) Date of Patent: Mar. 17, 2020

(54) ROBOT-ASSISTED ULTRASONIC OSTEOTOME POWERED SYSTEM

(71) Applicant: Beijing SMTP Technology Co., Ltd., Beijing (CN)

(72) Inventors: Qun Cao, Beijing (CN); Songtao Zhan, Beijing (CN); Xiaoming Hu, Beijing (CN)

(73) Assignee: Beijing SMTP Technology Co., Ltd., Beijing (CN)

( * ) Notice: Subject to any disclaimer, the term of this patent is extended or adjusted under 35 U.S.C. 154(b) by 0 days.

(21) Appl. No.: 16/515,339

(22) Filed: Jul. 18, 2019

(30) Foreign Application Priority Data

Feb. 14, 2019 (CN) .......................... 2019 1 0113251

(51) Int. Cl.
*A61F 2/46* (2006.01)
*A61B 17/16* (2006.01)
(Continued)

(52) U.S. Cl.
CPC .... *A61B 17/164* (2013.01); *A61B 17/320068* (2013.01); *A61B 34/30* (2016.02);
(Continued)

(58) Field of Classification Search
CPC combination set(s) only.
See application file for complete search history.

(56) References Cited

U.S. PATENT DOCUMENTS

| | | |
|---|---|---|
| 9,901,356 B2 | 2/2018 | Shen et al. |
| 10,117,713 B2 | 11/2018 | Barrera et al. |

(Continued)

FOREIGN PATENT DOCUMENTS

| | | |
|---|---|---|
| AU | 2017362480 A1 | 6/2019 |
| CN | 102085119 A | 6/2011 |

(Continued)

OTHER PUBLICATIONS

European Examination Report dated Jan. 30, 2020 in corresponding European Patent Application No. 19186563.3.

*Primary Examiner* — Sameh R Boles
(74) *Attorney, Agent, or Firm* — Veros Legal Solutions, LLP

(57) ABSTRACT

Disclosed is a robot-assisted ultrasonic osteotome powered system, comprising an ultrasonic osteotome powered system, a robot-assisted surgical system and a controller, wherein the osteotome powered system comprises an ultrasonic transducer for converting electrical energy into mechanical energy and an ultrasonic osteotome for delivering the mechanical energy to a bone; the robot-assisted surgical system comprises a base and a robot arm mounted to the base, the ultrasonic osteotome powered system is detachably connected to a movable end of the robot arm, and the robot arm is used to control the position of, the spatial angle of, and a force applied by a cutting end of the ultrasonic osteotome powered system to the bone to be cut; and the controller is communicatively connected to the ultrasonic osteotome powered system, for controlling a cutting power of the ultrasonic osteotome powered system, wherein the controller controls the output power of the ultrasonic osteotome powered system based on the remaining cutting thickness and the density of the bone, the type of an adjacent tissue, etc. The robot-assisted ultrasonic osteotome powered system of the present invention improves the safety and accuracy of systems for orthopedic surgery, particularly minimally invasive orthopedic surgery.

15 Claims, 2 Drawing Sheets

(51) Int. Cl.
*A61B 17/32* (2006.01)
*A61B 34/30* (2016.01)
*A61B 34/00* (2016.01)

(52) U.S. Cl.
CPC ........... *A61B 17/1642* (2013.01); *A61B 34/74* (2016.02); *A61B 2017/320052* (2013.01)

(56) References Cited

U.S. PATENT DOCUMENTS

| | | |
|---|---|---|
| 10,314,661 B2 | 6/2019 | Bowling et al. |
| 2013/0211421 A1 | 8/2013 | Abovitz et al. |
| 2015/0025549 A1 | 1/2015 | Kilroy et al. |
| 2015/0342618 A1 | 12/2015 | Nguyen |
| 2016/0066972 A1 | 3/2016 | Fuente |
| 2016/0354162 A1 | 12/2016 | Yen et al. |
| 2017/0056116 A1 | 3/2017 | Kostrzewski |
| 2017/0245955 A1 | 8/2017 | Bowling et al. |
| 2018/0049794 A1 | 2/2018 | Swayze et al. |
| 2018/0049821 A1 | 2/2018 | Shelton et al. |
| 2018/0092648 A1 | 4/2018 | Sun et al. |
| 2018/0110572 A1 | 4/2018 | Flatt |
| 2018/0168750 A1 | 6/2018 | Staunton et al. |

FOREIGN PATENT DOCUMENTS

| | | |
|---|---|---|
| CN | 101045015 B | 4/2012 |
| CN | 102783989 A | 11/2012 |
| CN | 106068104 A | 11/2016 |
| CN | 104207824 | 4/2017 |
| CN | 206315150 U | 7/2017 |
| CN | 104066389 | 11/2017 |
| CN | 108553768 A | 9/2018 |
| CN | 109259863 A | 1/2019 |
| CN | 109620415 A | 4/2019 |
| CN | 109745096 A | 5/2019 |
| EP | 3375400 A2 | 9/2018 |
| EP | 3342359 A1 | 2/2019 |
| JP | 2000217835 A | 8/2000 |
| KR | 20180038498 A | 4/2018 |
| WO | 2019130109 A1 | 7/2019 |

ROBOT-ASSISTED ULTRASONIC OSTEOTOME POWERED SYSTEM

TECHNICAL FIELD

The present invention relates to a robot-assisted ultrasonic osteotome powered system, wherein in particular, the ultrasonic osteotome powered system is accurately manipulated by a robot to perform surgical operations such as shaping and cutting on a bone, and is also usable for performing surgical operations such as shaping and cutting under an endoscope.

BACKGROUND ART

In the surgery of bone cutting, ultrasonic osteotome powered systems are often used for cutting. The ultrasonic osteotome powered systems convert electrical energy into mechanical energy through ultrasonic transducers, contacted bone tissues are completely destroyed by high-frequency ultrasonic vibration, and since the amplitude of vibration is generally about 100 μm, the damage to blood vessels and nerve tissues is weak. Therefore, they have high surgery safety in applications such as spinal and neurological surgery.

However, at present, the completion of the orthopedic and neurological surgery mainly relies on the doctor's manual operation of the ultrasonic osteotome powered systems. Since the doctors inevitably apply a longitudinal pressure substantially perpendicular to the bone during the operation, which manual operation has the problem of poor control over the longitudinal direction, when the ultrasonic osteotome powered systems cut through the bone, the longitudinal force applied by the doctors is too large to easily cause damage to the nerves, spinal cord and other tissues under the bone, and thus there is a certain risk of surgery. Moreover, due to the interaction between the ultrasonic vibration and the bone during the doctor's manual operation and the irregular curved shape of the bone, the ultrasonic osteotome powered systems will have a certain transverse vibration and displacement during cutting, which makes it difficult for the doctors to accurately control the ultrasonic osteotome powered systems, thereby resulting in a reduced cutting accuracy.

The robot-assisted surgical systems mainly rely on the sensing technology such as position sensors, angle sensors and force feedback sensors to control electric motors to achieve high-precision feedback control, which can effectively solve the problem of poor controllability and jitter existing in the doctor's manual operation and improve the safety of the surgical operation. However, the traditional robotic surgical systems lack effective bone tissue cutting tools, and can hardly complete the orthopedic surgery, especially the orthopedic minimally invasive surgery.

Therefore, there is a need for a robot-assisted ultrasonic osteotome powered system which integrates an ultrasonic osteotome powered system and a robotic surgical system.

SUMMARY OF THE INVENTION

It is an object of the present invention to provide a robot-assisted ultrasonic osteotome powered system integrated with an ultrasonic osteotome powered system and a robotic surgical system, the robot-assisted ultrasonic osteotome powered system being capable of at least partially solving or alleviating one or more of the following technical problems:

1) the force feedback problem of the ultrasonic osteotome powered system: at present, the bone cutting operation of the orthopedic surgery relies entirely on the doctor's clinical experience and feel, which is difficult to effectively transmit, especially in dangerous areas, for example, in the spinal and neurological surgery, since the mechanical properties of the patient's bone tissues are quite different, especially in some calcified areas the hardness is larger, whereas the other areas may have a less hardness due to calcium deficiency, relying on the doctor's experience alone to control the ultrasonic osteotome powered system is prone to the application of an excessive pressure, such that an ultrasonic cutter head quickly penetrates the bone, causing damage to the nerves, the spinal cord and other tissues under the bone, and resulting in medical accidents;

2) the cutting jitter problem of the ultrasonic osteotome powered system: if the ultrasonic osteotome powered system is used for cutting, when the doctor manipulates a handle to cut the bone tissues, due to the irregular curved shape of the bone, the vibration of the ultrasonic system easily causes the ultrasonic cutter head to slide transversely. Under the interaction between the ultrasonic vibration and the bone, the ultrasonic osteotome powered system has a certain transverse vibration. Therefore, the doctor needs to exert a large force to hold the handle to prevent the transverse movement of the cutter head. This transverse movement is likely to increase the size of the bone incision, somewhat affects the mechanical properties of the diseased site, and is more likely to cause transverse damage to the cutting site; and 3) the traditional orthopedic surgery robots lack effective bone tissue cutting tools, and still use the traditional bone tissue cutting tools, as a result, a huge pressure or rotational friction needs to be applied during cutting. Therefore, there is a big safety hazard, and it is difficult to successfully complete the orthopedic surgery, in particular, the orthopedic minimally invasive surgery, which also makes it difficult to widely apply the bone surgery robots using the traditional bone tissue cutting tools.

The present invention provides a robot-assisted ultrasonic osteotome powered system, comprising:

an ultrasonic osteotome powered system, comprising:
 an ultrasonic transducer for converting electrical energy into mechanical energy; and
 an ultrasonic osteotome for delivering the mechanical energy to a bone to be cut;
a robot-assisted surgical system, comprising:
 a base; and
 a robot arm having a fixed end mounted to the base, the ultrasonic osteotome powered system being detachably connected to a movable end of the robot arm, and the robot arm being used for controlling the position of, the spatial angle of, and a force applied by a cutting end of the ultrasonic osteotome powered system to the bone to be cut; and
a controller communicatively connected to the ultrasonic osteotome powered system, for controlling an output power of the ultrasonic osteotome powered system;
wherein the controller controls the output power P of the ultrasonic osteotome powered system according to the following equation:

$$P = P0 \times \alpha$$

where P0 is a reference output power of the ultrasonic osteotome powered system, and α is a power correction coefficient and α is less than or equal to 1, wherein α is determined, at least in part, from one or more of the following parameters:

1) the remaining cutting thickness of the bone, with α decreasing as the remaining cutting thickness decreases;

2) the density of the bone, with α decreasing as the density of the bone decreases;

3) the type of a tissue below the bone in a cutting direction, the type of the tissue including at least a blood vessel tissue, a spinal cord tissue, and a nerve tissue, wherein α for the blood vessel tissue is greater than or equal to α for the spinal cord tissue, and α for the spinal cord tissue is greater than or equal to α for the nerve tissue;

4) the temperature of the cutting end of the ultrasonic osteotome, with α decreasing as the temperature increases;

5) the type of the structure of the bone being cut, the type of the structure including at least a cortical bone and a cancellous bone, wherein α for the cortical bone is greater than or equal to α for the cancellous bone; and 6) the depth by which the ultrasonic osteotome has cut into the bone, with α decreasing as the depth increases.

BRIEF DESCRIPTION OF THE DRAWINGS

The technical solution of the present invention will be further described in detail below in conjunction with preferred embodiments and the accompanying drawings, in which.

DETAILED DESCRIPTION OF EMBODIMENTS

Figure 1:
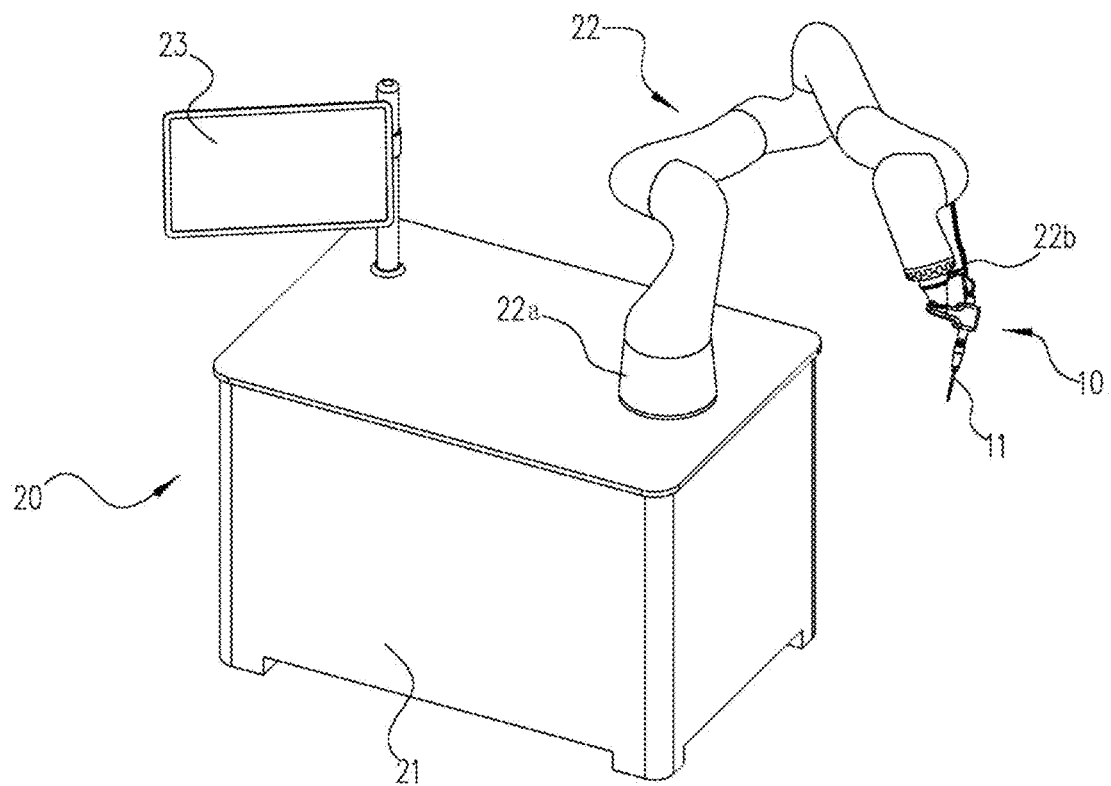
FIG. 1 is a schematic structural view of a robot-assisted ultrasonic osteotome powered system according to an embodiment of the present invention.

First of all, it should be noted that the basic structure, characteristics and advantages of the device for assisting orthopedic surgery of the present invention will be specifically described below by way of example, but all the descriptions are for illustrative purposes only and should not be construed as any limiting to the present invention. In addition, any single technical feature described or implied in the various embodiments mentioned herein, or any single technical feature shown or implied in the drawings, may still be in any combination or deleted among these technical features (or equivalents thereof) to obtain further embodiments of the present invention that may not be directly mentioned herein.

Figure 2:
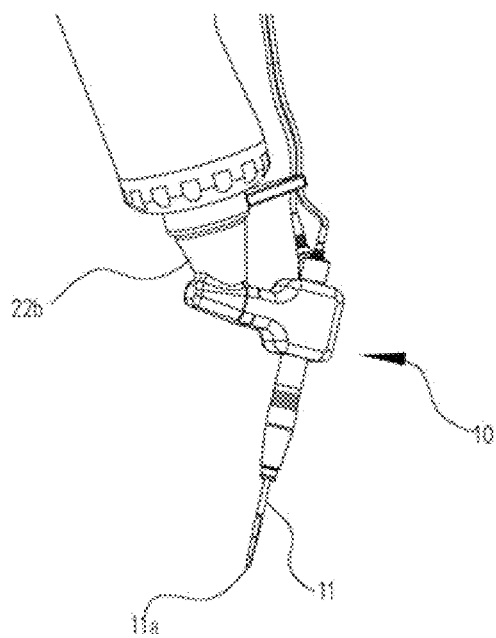
FIG. 2 is a partial enlarged view of the robot-assisted ultrasonic osteotome powered system shown in FIG. 1, showing a movable end of a robot arm of the robot-assisted surgical system and an ultrasonic osteotome powered system fixed to the end.

FIGS. 1 and 2 show a robot-assisted ultrasonic osteotome powered system 1 according to an embodiment of the present invention. The robot-assisted ultrasonic osteotome powered system 1 comprises an ultrasonic osteotome powered system 10, a robot-assisted surgical system 20, and a controller (not shown).

The ultrasonic osteotome powered system 10 comprises an ultrasonic transducer (not shown) for converting electrical energy into mechanical energy and an ultrasonic osteotome 11 for delivering the mechanical energy to a bone to be cut. The structure of the ultrasonic osteotome powered system 10 may be well known, for example, the ultrasonic osteotome powered system 10 may have the structures described in CN 109152577 A and CN 106068104 A.

The robot-assisted surgical system 20 comprises a base 21, a robot arm 22, and a display 23. A fixed end 22a of the robot arm 22 is mounted to the base 21, and the ultrasonic osteotome powered system 10 is fixedly connected to a movable end 22b of the robot arm 22. The robot arm 22 is used to control the position of, the spatial angle of, and a force applied by a cutting end 11a of the ultrasonic osteotome 11 of the ultrasonic osteotome powered system 10 to the bone to be cut. The structure of the robot-assisted surgical system 20 may be well known, for example, the robot-assisted surgical system 20 may be an articulated robot system (see, for example, CN 109171977 A) or a linear robot system (see, for example, CN 109152616 A). The robot-assisted surgical system 20 may have 2-7 degrees of freedom of movement, preferably 6 degrees of freedom of movement, and most preferably 7 degrees of freedom of movement. FIG. 2 shows a movable end 22b of the robot arm 22 and the ultrasonic osteotome powered system 10.

The controller is communicatively connected to the ultrasonic osteotome powered system 10 and the robot-assisted surgical system 20, for controlling the cutting power of the ultrasonic osteotome powered system 10. It is noted that the controller may be communicatively connected to the ultrasonic osteotome powered system 10 and the robot-assisted surgical system 20 in a wired or wireless manner. The cutting power of the ultrasonic osteotome powered system 10 is determined by the output power of the ultrasonic osteotome powered system 10 and the pressure applied to the bone to be cut by the cutting end 11a of the ultrasonic osteotome 11 of the ultrasonic osteotome powered system 10, and the output power of the ultrasonic osteotome powered system 10 is determined by the frequency and amplitude of vibration of the mechanical energy output by the ultrasonic transducer. Therefore, the cutting power can be adjusted by adjusting the frequency and/or amplitude of the output vibration of the ultrasonic osteotome powered system 10, and the cutting power can also be adjusted by adjusting the pressure applied to the bone to be cut by the cutting end 11a of the ultrasonic osteotome 11. It will be understood by those skilled in the art that the controller may also be communicatively connected only to the ultrasonic osteotome powered system 10, whereas the robot-assisted surgical system 20 may be controlled by another separate controller. In this case, it is preferred that the controller for controlling the ultrasonic osteotome powered system 10 and the controller for controlling the robot-assisted surgical system 20 are capable of communicating with each other to coordinately control the ultrasonic osteotome powered system 10 and the robot-assisted surgical system 20.

In the above-described robot-assisted ultrasonic osteotome powered system 1, the controller controls the output power P of the ultrasonic osteotome powered system 10 according to the following equation:

$$P = P0 \times \alpha$$

where P0 is a reference output power of the ultrasonic osteotome powered system 10, and α is a power correction coefficient and α is less than or equal to 1, wherein α is determined, at least in part, from one or more of the following parameters:

1) the remaining cutting thickness of the bone, with α decreasing as the remaining cutting thickness decreases, to avoid still applying a large output power when the remaining cutting thickness is small, which causes the ultrasonic osteotome to quickly penetrate the bone to cause damage to the tissues such as blood vessels, nerves, and the spinal cord below the bone;

2) the density of the bone, with α decreasing as the density of the bone decreases;

3) the type of a tissue below the bone in a cutting direction, the type of the tissue including at least a blood vessel tissue, a spinal cord tissue, and a nerve tissue, wherein α for the blood vessel tissue is greater than or equal to α for the spinal cord tissue, and α for the spinal cord tissue is greater than or equal to α for the nerve tissue; as an example, the type of the tissue may be determined by anatomy and is input into the controller before the start of surgery, in this way, the value of the power correction coefficient α is more finely set, which can avoid or reduce the risk of adversely affecting the tissues below the bone in the cutting direction while maintaining a suitable cutting speed;

4) the temperature of the cutting end of the ultrasonic osteotome, with α decreasing as the temperature increases, thereby avoiding the generation of high temperature to adversely affect non-targeted cutting tissues such as the nerves, the blood vessels, and the spinal cord, etc.;

5) the type of the structure of the bone being cut, the type of the structure including at least a cortical bone and a cancellous bone, wherein α for the cortical bone is greater than or equal to α for the cancellous bone, and by distinguishing the types of the structures of the bone being cut, such as the cortical and cancellous bones, the output power can be more finely controlled; and 6) the depth by which the ultrasonic osteotome has cut into the bone, with α decreasing as the depth increases, wherein when the ultrasonic osteotome has cut into the bone tissue by a great depth, a liquid flow is difficult to be cooled, and the heat generated is also not easily dissipated from the bone tissues by convection and radiation, so that it is likely to form a local high-temperature region, which is disadvantageous to the bones and the nerves. By reducing the value of the power correction coefficient α with the increase of the cutting depth, the formation of a local high-temperature region can be avoided.

It should be noted that the reference output power of the ultrasonic osteotome powered system 10 may be a fixed value or a value that varies depending on the type of the ultrasonic osteotome 11 used. The type of ultrasonic osteotome 11 herein includes, but is not limited to, the shape, the material, the dimensions of the cutting end of the ultrasonic osteotome, and whether the ultrasonic osteotome 11 has a cooling structure. As a preferred embodiment, the ultrasonic osteotome powered system 10 and/or the ultrasonic osteotome 11 may comprise an electronic identification tag, such as a radio frequency identification (RFID) tag, such that after the ultrasonic osteotome powered system 10 and/or the ultrasonic osteotome 11 are/is mounted to the robot-assisted surgical system 20, the controller can read the electronic identification tag to identify the characteristic parameters of the ultrasonic osteotome powered system 10 and/or the ultrasonic osteotome 11 and then selects suitable control parameters, such as the frequency and amplitude of vibration of the ultrasonic osteotome powered system 10 and the pressure applied to the bone to be cut by the cutting end 11a of the ultrasonic osteotome 11. In addition, when the controller cannot read the electronic identification tag(s) of the ultrasonic osteotome powered system 10 and/or the ultrasonic osteotome 11 or when the electronic identification tag(s) read from the ultrasonic osteotome powered system 10 and/or the ultrasonic osteotome 11 do(es) not match, the controller displays warning information to the doctor via the display 23 and prohibits the entire robot-assisted ultrasonic osteotome powered system 1 from operating.

The display 23 can also display the information such as a 3D model of the bone to be cut, the position and orientation of the cutting end 11a of the ultrasonic osteotome 11, the remaining cutting thickness of the bone, the density of the bone, the type of the tissues below the bone in the cutting direction, the output power, the force F applied to the ultrasonic osteotome by the robot arm, and the cutting power, so that the doctor and/or other operators can monitor the surgery procedure in real time.

As a possible preferred embodiment, the output power correction coefficient α is further determined by the shape of the cutting end 11a of the ultrasonic osteotome 11 and/or by whether the ultrasonic osteotome 11 has a cooling structure, wherein at the same cutting power, the faster the cutting speed for the shape of the cutting end, the smaller the output power correction coefficient α; and wherein the correction coefficient α for the ultrasonic osteotome with the cooling structure is larger than the correction coefficient α for the ultrasonic osteotome without the cooling structure. As is known to those skilled in the art, the ultrasonic osteotome 11, in particular the cutting end 11a of the ultrasonic osteotome 11, may have different shapes, dimensions and structures (e.g. with or without a cooling structure). The ultrasonic osteotomes having different shapes, dimensions and structures are disclosed in the applicant's patent application publications CN 107744401 A, CN 107582128 A, CN 107518929 A, CN 107320151 A, CN 206183334 U, CN 205234577 U, CN 203354609 U, CN 202920294 U, CN 202821536 U, CN 202740089 U, CN 202740088 U, CN 102475568 A, CN 202161377 U, CN 202146334 U, etc. Therefore, the details of the ultrasonic osteotome 11 will not be described herein. Generally, at the same cutting power, the cutting end 11a having cutting teeth (see, for example, CN 205234577 U described above) cuts the bone faster than the cutting end 11a without the cutting teeth, and the ultrasonic osteotome 11 with a faster cutting speed uses the correction coefficient α with a smaller value, which enables a more precise and smoother control over the cutting process. In addition, the ultrasonic osteotome 11 having no cooling structure produces a higher temperature in the cutting process and has a greater heat risk to the surrounding tissues than the ultrasonic osteotome 11 having a cooling structure (see, for example, CN 107518929 A described above). Therefore, by setting the correction coefficient α for the ultrasonic osteotome 11 having no cooling structure to be smaller than the correction coefficient α for the ultrasonic osteotome 11 having the cooling structure, it is possible to prevent the temperature of the cutting region from being excessively increased to affect the surrounding tissues.

As described above, in addition to controlling the ultrasonic osteotome powered system 10, the controller may also be communicatively connected to the robot-assisted surgical system 20 in a wired or wireless manner, for controlling the position of, the spatial angle of, and the force applied to the cutting end 11a of the ultrasonic osteotome 11 by the robot arm 22. The force herein primarily refers to a longitudinal force applied by the cutting end 11a to the bone substantially along the normal to the cutting site, which determines the cutting power together with the output power of the ultrasonic osteotome powered system 10. Preferably, the controller controls the force (longitudinal force) F applied substantially in the cutting direction to the cutting end 11a of the ultrasonic osteotome 11 by the robot arm 22 according to the following equation:

$$F = F_0 \times \beta$$

where F0 is a reference longitudinal force applied by the robot arm 22 to the ultrasonic osteotome 11, and β is a force correction coefficient and β is less than or equal to 1, wherein β is determined, at least in part, from one or more of the following parameters:

1) the remaining cutting thickness of the bone, with β decreasing as the remaining cutting thickness decreases, to avoid still applying a large cutting force when the remaining cutting thickness is small, which causes the ultrasonic osteotome to quickly penetrate the bone to cause damage to the tissues such as blood vessels, nerves, and the spinal cord below the bone;

2) the density of the bone, with β decreasing as the density of the bone decreases;

3) the type of a tissue below the bone in the cutting direction, the type of the tissue including at least a blood vessel tissue, a spinal cord tissue, and a nerve tissue, wherein β for the blood vessel tissue is greater than or equal to β for the spinal cord tissue, and β for the spinal cord tissue is greater than or equal to β for the nerve tissue; as an example, the type of the tissue may be determined by anatomy, in this way, the value of the force correction coefficient β is more finely set, which can avoid or reduce the risk of adversely affecting the tissues below the bone in the cutting direction while maintaining a suitable cutting speed;

4) the temperature of the cutting end 11a of the ultrasonic osteotome 11, with β decreasing as the temperature increases, thereby avoiding the generation of high temperature to adversely affect non-targeted cutting tissues such as the nerves, the blood vessels, and the spinal cord;

5) the type of the structure of the bone being cut, the type of the structure including at least a cortical bone and a cancellous bone, wherein β for the cortical bone is greater than or equal to β for the cancellous bone; and by distinguishing the types of the structures of the bone being cut, such as the cortical and cancellous bones, the magnitude of the force can be more finely controlled; and 6) the depth by which the ultrasonic osteotome has cut into the bone, with β decreasing as the depth increases, wherein when the ultrasonic osteotome has cut into the bone tissues by a great depth, a liquid flow is difficult to be cooled, and the heat generated is also not easily dissipated from the bone tissues by convection and radiation, so that it is likely to form a local high-temperature region, which is disadvantageous to the bones and the nerves. By reducing the value of the force correction coefficient β with the increase of the cutting depth, the formation of a local high-temperature region can be avoided.

As a preferred embodiment, similar to the output power correction coefficient α, the force correction coefficient β may be further determined by the shape of the cutting end 11a of the ultrasonic osteotome 11 and/or by whether the ultrasonic osteotome 11 has a cooling structure, wherein at the same cutting power, the faster the cutting speed for the shape of the cutting end, the smaller the β; and wherein β for the ultrasonic osteotome with the cooling structure is larger than β for the ultrasonic osteotome without the cooling structure.

The ultrasonic osteotome powered system 10 comprises a temperature sensor (not shown) for detecting the temperature of the cutting end 11a and transmitting a signal indicative of the temperature to the controller. The ultrasonic osteotome powered system 10 and/or the robot-assisted surgical system 20 comprise(s) a force sensor (not shown) for detecting the longitudinal force applied to the bone by the cutting end 11a of the ultrasonic osteotome 11 and transmitting the signal indicative of the longitudinal force to the controller. Additionally, the force sensor can also detect a transverse force applied by the robot arm to the ultrasonic osteotome powered system 10 that is substantially perpendicular to the longitudinal force and transmit a signal indicative of the transverse force to the controller, so as to better control the transverse force, thereby improving the stability of control over the position and the spatial angle of the cutting end. By detecting the temperature, the longitudinal force, and the transverse force of the cutting end during cutting, the controller can more accurately control the entire cutting process, thereby improving the safety of the surgery.

Figure 3:
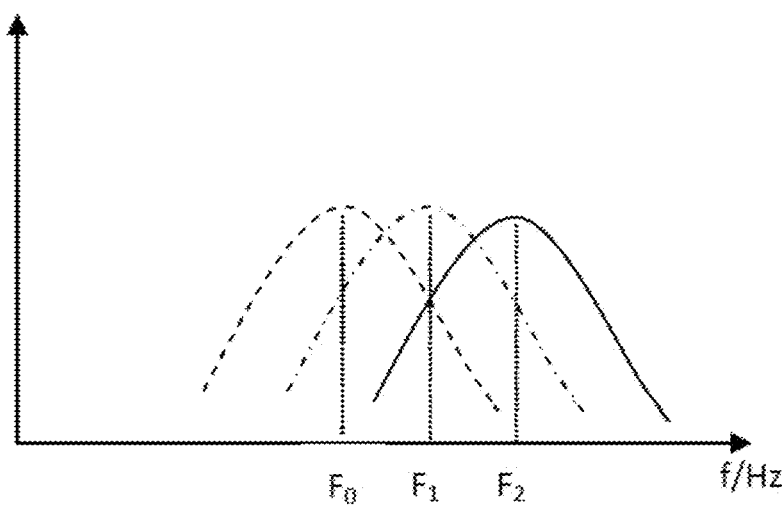
FIG. 3 shows the magnitudes of the frequency offsets of the ultrasonic osteotome powered system caused by different bone structures (i.e., cortical and cancellous bones)

As an example, the controller can determine whether the bone portion being cut is the cortical bone or the cancellous bone by detecting the magnitude of a frequency offset of the ultrasonic osteotome powered system 10 caused by the bone during cutting. As shown in FIG. 3, due to the difference in the ultrasonic vibration characteristics of the cancellous bone and the cortical bone, when the ultrasonic osteotome powered system 10 applies pressure to cut the two bone tissues, the magnitudes of the frequency offsets of the ultrasonic osteotome powered system 10 caused by the bone tissues are different. In FIG. 3, F0 is the characteristic resonance frequency of the ultrasonic osteotome powered system 10, F1 is the characteristic resonance frequency of the ultrasonic osteotome powered system 10 when cutting the cancellous bone, and F2 is the characteristic resonance frequency of the ultrasonic osteotome powered system 10 when cutting the cortical bone. By determining whether the bone tissue being cut is a cortical bone or a cancellous bone, the controller can more appropriately control the output power and the longitudinal force applied by the robot arm 22 to the ultrasonic osteotome 11.

In order to determine the remaining cutting thickness of the bone and to control the position, the spatial angle, etc. of the cutting end 11a of the ultrasonic osteotome 11 with respect to the bone, the controller comprises a data receiving portion for receiving external input data to obtain the three-dimensional model and/or dimension data of the bone to be cut, for example, the external input data may include CT data, MR data, etc. of the bone to be cut, which is capable of reflecting the three-dimensional structure of the bone. In addition, the controller may also receive density data of the bone with the data receiving portion.

Figure 4:
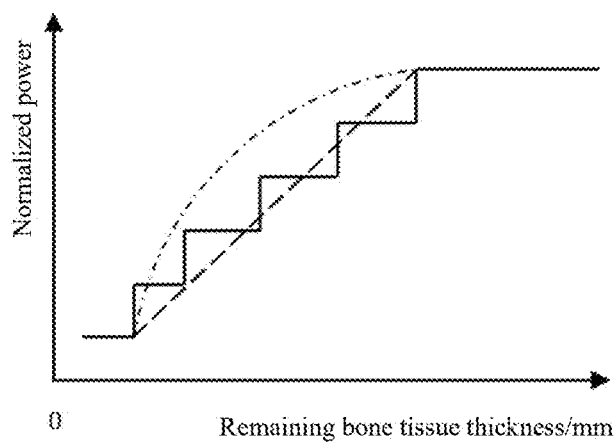
FIG. 4 shows a typical curve of the normalized cutting power level over the remaining bone tissue thickness.

Preferably, the output power and/or the force applied to the bone to be cut by the ultrasonic osteotome 11 are/is in a linear relationship or in a parabolic relationship or in an exponentially decaying relationship with the remaining cutting thickness. FIG. 4 shows a typical curve of the normalized cutting power level over the remaining bone tissue thickness, wherein the output power magnitude may be in a linear, or parabolic relationship with the remaining bone tissue thickness. The typical curve of the pressure exerted by the robot arm 22 over the remaining bone tissue thickness is similar to the output power curve shown in FIG. 4, and may also be in an exponentially decaying relationship.

As a preferred embodiment, the controller starts to control the output power and the longitudinal force only when the remaining cutting thickness is less than a threshold thickness (e.g., 2-5 mm, preferably 2 mm).

Figure 5:
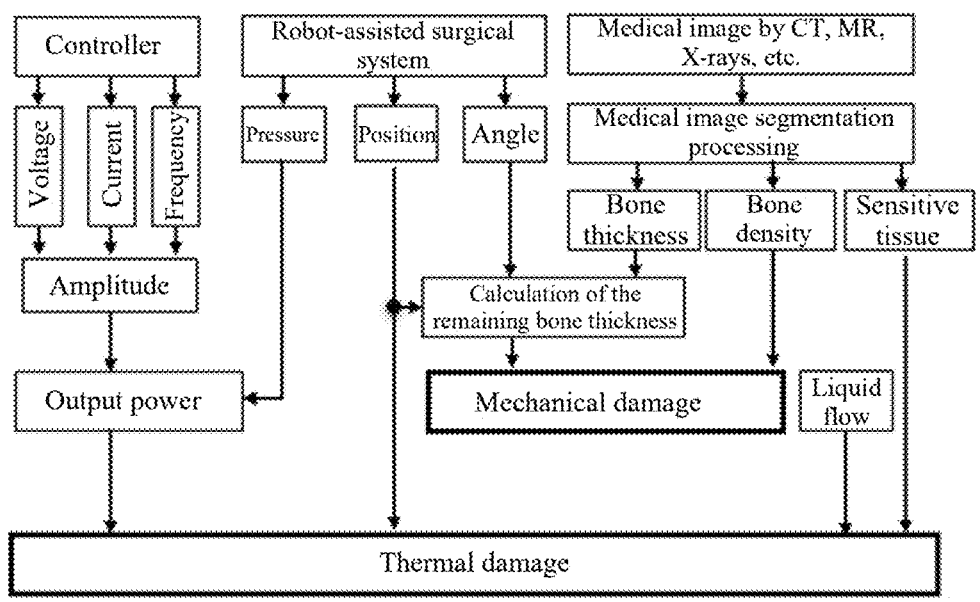
FIG. 5 shows a schematic diagram of the operation of the robot-assisted ultrasonic osteotome powered system of the present invention.

FIG. 5 is a schematic view showing the operation process of the robot-assisted ultrasonic osteotome powered system 1 of the present invention. Before the operation, a three-dimensional image of the patient's bone is reconstructed by CT or MR, the three-dimensional shape, the thickness, the density and other related parameters of the bone tissue to be cut are extracted, and these parameters are input into the controller of the robot-assisted ultrasonic osteotome powered system 1, so as to achieve a three-dimensional registration of the cutting end 11a of the ultrasonic osteotome 11 with the bone. In the bone cutting process, the controller controls the output power of the ultrasonic osteotome powered system 10, and the position and the spatial orientation of the cutting end 11a of the ultrasonic osteotome 11, and controls the force F applied to the ultrasonic osteotome by the robot arm in the manner described above, thereby avoiding or at least significantly reducing the risk of mechanical and thermal damage to the bone and sensitive tissues (e.g., blood vessels, nerves, or bone marrow) near the bone to achieve safe operation of the surgery.

The robot-assisted ultrasonic osteotome powered system of the present invention significantly improves the safety of use of the ultrasonic osteotome powered system by controlling both the pressure and the vibration output power. Specifically, the main function of the pressure control is to avoid mechanical damage caused by the rupture of the bone tissues directly due to the application of excessive pressure when the remaining bone tissues are relatively thin (i.e., the remaining cutting thickness is relatively small). The function of controlling the vibration output power consists in that when the cutting depth is relatively deep and the bone is relatively hard, the relatively large cutting power may cause thermal damage to the nerves, blood vessels and other tissues adjacent to the bone, and when the remaining bone tissue is relatively thin (i.e., the remaining cutting thickness is relatively small), the cutting effect under the same power conditions can be improved by adjusting the resonance frequency of the ultrasonic osteotome powered system.

Those skilled in the art will appreciate that the present invention may have various other embodiments, without departing from the spirit and scope of the present invention, a person skilled in the art will be able to make various changes and modifications in accordance with the present invention, and these respective changes and modifications are intended to fall within the scope of protection of the appended claims of the present invention. For example, although only the parameters, such as the remaining cutting thickness of the bone, the density of the bone, the type of the tissues below the bone, the temperature of the cutting site, the type of the structure of the bone, and the cut depth, affecting the power correction coefficient $\alpha$ and the force correction coefficient $\beta$ are listed above, it should be understood that the technical solutions for adjusting the power correction coefficient $\alpha$ and the force correction coefficient $\beta$ using other parameters directly or indirectly related to these parameters should also fall within the scope of protection defined by the appended claims.

The invention claimed is:

1. A robot-assisted ultrasonic osteotome powered system, comprising:
   an ultrasonic osteotome powered system, comprising:
      an ultrasonic transducer for converting electrical energy into mechanical energy; and
      an ultrasonic osteotome for delivering the mechanical energy to a bone;
   a robot-assisted surgical system, comprising:
      a base; and
      a robot arm having a fixed end mounted to the base, the ultrasonic osteotome powered system being detachably connected to a movable end of the robot arm, and the robot arm being used for controlling a position of, a spatial angle of, and a force applied by a cutting end of the ultrasonic osteotome powered system to the bone; and
   a controller communicatively connected to the ultrasonic osteotome powered system, for controlling an output power of the ultrasonic osteotome powered system;
   wherein the controller controls the output power P of the ultrasonic osteotome powered system according to an equation comprising:

$$P = P0 \times \alpha$$

wherein P0 is a reference output power of the ultrasonic osteotome powered system, and $\alpha$ is a power correction coefficient and $\alpha$ is less than or equal to 1, wherein $\alpha$ is determined, at least in part, from one or more of parameters comprising:
   1) a remaining cutting thickness of the bone, with $\alpha$ decreasing as the remaining cutting thickness decreases;
   2) a density of the bone, with $\alpha$ decreasing as the density of the bone decreases;
   3) a type of a tissue below the bone in a cutting direction, the type of the tissue including at least a blood vessel tissue, a spinal cord tissue, and a nerve tissue, wherein $\alpha$ for the blood vessel tissue is greater than or equal to $\alpha$ for the spinal cord tissue, and $\alpha$ for the spinal cord tissue is greater than or equal to $\alpha$ for the nerve tissue;
   4) a temperature of the cutting end of the ultrasonic osteotome, with $\alpha$ decreasing as the temperature increases;
   5) a type of the structure of the bone being cut, the type of the structure including at least a cortical bone and a cancellous bone, wherein $\alpha$ for the cortical bone is greater than or equal to $\alpha$ for the cancellous bone; and
   6) a depth by which the ultrasonic osteotome has cut into the bone, with $\alpha$ decreasing as the depth increases.

2. The robot-assisted ultrasonic osteotome powered system according to claim 1, wherein $\alpha$ is further determined by a shape of the cutting end of the ultrasonic osteotome and/or by whether the ultrasonic osteotome has a cooling structure, wherein at a same cutting power, the faster a cutting speed for the shape of the cutting end, the smaller the $\alpha$; and wherein $\alpha$ for the ultrasonic osteotome with the cooling structure is larger than $\alpha$ for the ultrasonic osteotome without the cooling structure.

3. The robot-assisted ultrasonic osteotome powered system according to claim 1, wherein the controller is further communicatively connected to the robot-assisted surgical system, for controlling the position of, the spatial angle of, and the force applied to the ultrasonic osteotome by the robot arm.

4. The robot-assisted ultrasonic osteotome powered system according to claim 3, wherein the controller controls a force F applied substantially in the cutting direction to the cutting end of the ultrasonic osteotome by the robot arm according to an equation comprising:

$$F = F0 \times \beta$$

wherein F0 is a reference force applied by the robot arm to the ultrasonic osteotome, and $\beta$ is a force correction coefficient and $\beta$ is less than or equal to 1, wherein $\beta$ is determined, at least in part, from one or more of parameters comprising:
1) the remaining cutting thickness of the bone, with $\beta$ decreasing as the remaining cutting thickness decreases;
2) the density of the bone, with $\beta$ decreasing as the density of the bone decreases;
3) the type of a tissue below the bone in the cutting direction, the type of the tissue including at least a blood vessel tissue, a spinal cord tissue, and a nerve tissue, wherein β for the blood vessel tissue is greater than or equal to β for the spinal cord tissue, and β for the spinal cord tissue is greater than or equal to β for the nerve tissue;

4) the temperature of the cutting end of the ultrasonic osteotome, with β decreasing as the temperature increases;

5) the type of the structure of the bone being cut, the type of the structure including at least a cortical bone and a cancellous bone, wherein β for the cortical bone is greater than or equal to β for the cancellous bone; and 6) the depth by which the ultrasonic osteotome has cut into the bone, with β decreasing as the depth increases.

5. The robot-assisted ultrasonic osteotome powered system according to claim 4, wherein β is further determined by the shape of the cutting end of the ultrasonic osteotome and/or by whether the ultrasonic osteotome has a cooling structure, wherein at the same cutting power, the faster a cutting speed for the shape of the cutting end, the smaller the β; and wherein β for the ultrasonic osteotome with the cooling structure is larger than β for the ultrasonic osteotome without the cooling structure.

6. The robot-assisted ultrasonic osteotome powered system according to claim 1, wherein the ultrasonic osteotome powered system comprises a temperature sensor for detecting the temperature of the cutting end and transmitting a signal indicative of the temperature to the controller.

7. The robot-assisted ultrasonic osteotome powered system according to claim 1, wherein the ultrasonic osteotome powered system and/or the robot-assisted surgical system comprise(s) a force sensor for detecting the force applied to the bone by the cutting end of the ultrasonic osteotome and transmitting a signal indicative of the force to the controller.

8. The robot-assisted ultrasonic osteotome powered system according to claim 1, wherein the controller determines whether the bone portion being cut is the cortical bone or the cancellous bone by detecting a magnitude of a frequency offset of the ultrasonic osteotome powered system caused by the bone during cutting.

9. The robot-assisted ultrasonic osteotome powered system according to claim 1, wherein the controller comprises a data receiving portion for receiving external input data to obtain a three-dimensional model and/or dimension data and/or density data of the bone to be cut.

10. The robot-assisted ultrasonic osteotome powered system according to claim 9, wherein the external input data includes one or more of CT data, MR data, and density data of the bone to be cut.

11. The robot-assisted ultrasonic osteotome powered system according to claim 1, wherein the controller controls the output power by changing an amplitude and/or frequency of vibrations of the ultrasonic osteotome powered system.

12. The robot-assisted ultrasonic osteotome powered system according to claim 1, wherein the output power and/or the force applied to the bone to be cut by the ultrasonic osteotome are/is in a linear relationship, a parabolic relationship, or an exponentially decaying relationship with the remaining cutting thickness.

13. The robot-assisted ultrasonic osteotome powered system according to claim 1, wherein the controller starts to control the output power and/or the force only when the remaining cutting thickness is less than a threshold thickness.

14. The robot-assisted ultrasonic osteotome powered system according to claim 1, wherein the ultrasonic osteotome powered system and/or the ultrasonic osteotome are/is replaceable.

15. The robot-assisted ultrasonic osteotome powered system according to claim 1, wherein the ultrasonic osteotome powered system and/or the ultrasonic osteotome comprise(s) an electronic identification tag, which can be read by the controller to identify characteristic parameters of the ultrasonic osteotome powered system and/or the ultrasonic osteotome.

\* \* \* \* \*